United States Patent [19]

Warner et al.

[11] 4,244,876

[45] Jan. 13, 1981

[54] ACETAL-ACID COMPOSITIONS

[75] Inventors: Glenn H. Warner, St. Albans; Louis F. Theiling, Charleston, both of W. Va.; Marvin G. Freid, Putnam Valley, N.Y.

[73] Assignee: Union Carbide Corporation, New York, N.Y.

[21] Appl. No.: 961,714

[22] Filed: Nov. 17, 1978

[51] Int. Cl.$^3$ .................. C07D 309/06; C07C 41/46; C07C 47/198
[52] U.S. Cl. .................. 260/345.9 R; 252/8.55 D; 568/580; 568/603; 568/421; 568/497
[58] Field of Search .................. 260/345.9 R, 602; 568/580, 603

[56] References Cited

U.S. PATENT DOCUMENTS

| | | | |
|---|---|---|---|
| 2,546,018 | 3/1951 | Smith et al. | 260/345.9 R |
| 2,801,216 | 7/1957 | Yoder et al. | 260/345.9 R |
| 2,931,837 | 4/1960 | Stansbury, Jr. et al. | 260/345.9 R |
| 3,023,243 | 2/1962 | Stansbury, Jr. et al. | 260/345.9 R |
| 3,480,678 | 11/1969 | Thweatt | 260/345.9 R |

OTHER PUBLICATIONS

Harries et al., Chem. Ber., 41, 1701 (1908).
Mutterer et al., Bull Soc. Chim. France, 12, 4478 (1969).
Kankaanpera, Acta Chem. Scan., 23, 1465 (1969).

*Primary Examiner*—Nicky Chan
*Attorney, Agent, or Firm*—Gary L. Wamer; Stanley Ktorides

[57] ABSTRACT

A storage stable composition of glutaraldehyde acetals and an organic acidic catalyst, which can be converted to glutaraldehyde at the site and upon demand, by the addition of water.

8 Claims, No Drawings

ACETAL-ACID COMPOSITIONS

BACKGROUND OF THE INVENTION

For many years, aqueous solutions of glutaraldehyde have been used as a biocide in a number of applications. Among the most important of such applications is the use of glutaraldehyde to control sulfate reducing bacteria contaminating oil wells. In this application, glutaraldehyde in concentrations of from 10 to 50 ppm is added to injection water used for secondary oil recovery.

In the oil industry glutaraldehyde is employed as either a 25 or 50 percent aqueous solution because pure glutaraldehyde is inherently unstable and polymerizes to a hard glass on standing. Extensive deterioration is known to occur when a 50 percent aqueous glutaraldehyde solution is held at 60° C. for 2 to 3 weeks, the average outdoor summer temperature of many important oil producing areas.

Aqueous glutaraldehyde solutions are also expensive to ship because of the large amount of water involved. Thus, a composition which would reduce the amount of inactive material shipped and at the same time increase the shelf-life of glutaraldehyde at higher temperatures would be highly desirable.

SUMMARY OF THE INVENTION

It has now been found that mixtures of glutaraldehyde acetals and certain soluble acidic catalysts can be stored at elevated temperatures with little significant deterioration and, when combined with water at the location of use, form glutaraldehyde.

DESCRIPTION OF THE INVENTION

This invention relates to a storage stable mixture of one or more glutaraldehyde acetals and an acid catalyst. This mixture may be stored for extended periods at elevated temperatures above about 38° C. and can then be easily converted to glutaraldehyde by the addition of water.

The acetals suitable for use in this invention are certain dialkoxypentanals, tetraalkoxypentanes, 2,6-dialkoxy tetrahydropyrans or mixtures thereof. The compounds are known; however, it was heretofore not known that they would be stable in mixtures with organic acid and would then hydrolyze rapidly at ambient temperature upon the addition of water to produce glutaraldehyde in high yields. These findings were completely unexpected and unobvious. Also known is the manner in which the acetals are produced.

Thus, it is known that the reaction of a 2-alkoxy dihydropyran with an alkanol of the formula ROH, wherein R is an alkyl group having from 1 to 6 carbon atoms, preferably 1 to 3 carbon atoms, will produce a mixture of the corresponding 2,6-dialkoxy tetrahydropyran, dialkoxypentanal (or diacetal) and tetraalkoxypentane (or tetraacetal); which mixture can be subsequently separated into its separate components by known conventional procedures. One can also react the 2-alkoxy-3,4-dihydropyran, with a glycol of the formula HOR'OH, wherein R' is an alkylene group having from 2 to 6 carbon atoms, preferably 2 or 3 carbon atoms, under similar conditions. In this reaction a catalyst is generally used and any of the known catalysts can be employed. The acetalization reaction is generally carried out at an elevated temperature up to about 100° C., as is known to those skilled in the art.

Illustrative of some of the 2-alkoxy-3,4-dihydropyrans which can be used to produce the acetals mixture one can mention 2-methoxy-3,4-dihydropyran, 2-ethoxy-3,4-dihydropyran and the like. The preferred is 2-methoxy-3,4-dihydropyran.

The alcohols that can be reacted with the 2-alkoxy-3,4-dihydropyran include methanol, ethanol, propanol, isopropanol, or other aliphatic alcohols. The preferred are methanol and ethanol.

Illustrative of suitable glycols one can mention ethylene glycol, 1,2-propylene glycol, 1,3-propylene glycol, 1,4-butanediol and the like. The preferred are ethylene and propylene glycols.

Illustrative of the acetals or pyran derivatives that are used to produce the storage stable compositions of this invention one can mention 1,1,5,5,-tetramethoxy pentane, 5,5,-dimethoxy pentanal and cis- and trans-2,6-dimethoxy tetrahydropyran. Among the most preferred are the methoxy acetals and pyran derivatives because the mixtures produced from methanol, which contain the methoxy substituent, hydrolyze to glutaraldehyde at a faster rate under the same reaction conditions. When the conversion rate to an active biocidal solution of glutaraldehyde is not critical, other dihydropyrans and other aliphatic alcohols or glycols may be used.

The acid used in the storage stable compositions of this invention is a soluble organic acid, saturated or unsaturated, containing up to 6 carbon atoms, which functions as a hydrolysis catalyst when water is added to the acetal-acid mixture. It can be a monocarboxylic acid or polycarboxylic acid and can contain substituents which do not interfere with the components or the reaction. The concentration of the organic acid in the acetal mixture is about 0.25 to 2.5 weight percent, preferably from about 0.4 to 1.5 weight percent and produces a solution with a pH of from 1.5 to 2.2 after the water is added. The preferred acids are those which are soluble in the acetal mixture to the extent of at least about 0.25 weight percent thereof. Any of the known organic acids can be used that possess this solubility property. They are well known to those skilled in the art and include formic acid, acetic acid, citric acid, fumaric acid, the organo sulfuric acids, the organo sulfonic acids, and the like. One can use a single organic acid or a mixture of organic acids; further one can include some inorganic acid, such as boric acid, phosphoric acid and the like, if one wishes. The storage stable composition is prepared by mixing the organic acid with the acetals.

In a typical embodiment, a mixture of cis- and trans-2,6-dimethoxy tetrahydropyran, 5,5-dimethoxypentanal and 1,1,5,5,-tetramethoxypentane is produced by the reaction of 2-methoxy-3,4-dihydropyran with methanol in contact with a strong acid ion exchange resin as catalyst. Methanol and the catalyst are charged to a reactor and 2-methoxy-3,4-dihydropyran is added and this mixture is maintained at the reaction temperature for an additional period of time after the addition is completed until the reaction is completed. The insoluble catalyst is then removed by filtration and the organic acid is added to the acetal mixture. This acetal-organic acid mixture can now be stored for an extended period at normal storage conditions with essentially no noticeable change in the product composition. As required, the mixture is converted to glutaraldehyde by addition of water.

The compositions of this invention are of great utility in the production of glutaraldehyde and its employment as a biocide. Because of the unexpected, and unobvious excellent stability of the compositions, they can be stored for long periods and at higher temperatures than can the presently available aqueous commercial solutions of glutaraldehyde. This property is particularly advantageous when glutaraldehyde is employed as a biocide in oil recovery operations because many oil wells are located in remote areas which have high-temperature climates. Another advantage of this invention is the reduced shipping costs resulting from the elimination of the need to transport water which is presently required because, due to the instability of pure glutaraldehyde, at least a 50 percent aqueous solution of glutaraldehyde must be used. Still another advantage of this invention is the improved materials handling conditions which result. Further, the handling of glutaraldehyde is a disagreeable task due to the pungent, irritating nature of glutaraldehyde vapors. The odor of the mixtures that are the compositions of this invention, while evident, is neither pungent nor unduly unpleasant to work with.

It was completely unexpected and unobvious to find that a mixture of glutaraldehyde acetals and a soluble acid could be stored without degradation and, subsequently, could be easily converted to biocidally active glutaraldehyde by the addition of water.

The following examples serve to further illustrate the invention:

EXAMPLE 1

There were charged to a reaction vessel, 31.2 grams of methanol, 64 grams of 2-ethoxy-3,4-dihydropyran and 10 grams of a strong acid ion exchange resin (Amberlyst-15 ®). The mixture was stirred with a magnetic stirrer for 60 minutes. The temperature of the reaction mixture rose rapidly to 75° C. within the first 10 minutes of stirring and then declined. After 60 minutes of stirring, a sample of the reaction mixture was analyzed by gas liquid chromatography. The analysis showed complete conversion of the dihydropyran to a mixture of acetals with over 50 percent of the reaction product being cis- and trans-2,6-dialkoxy tetrahydropyran.

The reaction product was stripped at atmospheric pressure and at a kettle temperature of from 120° C. to 150° C. to remove the excess methanol and the residual material distilled through a goose-neck at reduced pressure to give a mixture of acetals boiling 30°-96° C./2 mm. A 10 gram sample of this solvent free composition, having a pH of from 6.5 to 6.8 when mixed with water as a 10% solution, was mixed with 90 grams of water and 1 drop of acetic acid and stirred for 24 hours. After this time the mixture had a pH of 3.3 and a gas liquid chromatographic analysis showed complete conversion of the acetals to glutaraldehyde.

EXAMPLE 2

To a mixture of 130.7 kilograms of anhydrous methanol and 3.2 kilograms of Amberlyst-15 ® resin, there was added over a 10 hour period 232.5 kilograms of 2-methoxy-3,4-dihydropyran. The temperature of the reaction mixture was held at 40° C. throughout the feed period by external cooling. After the 10 hour feed period was completed, the mixture was held at 40° C. for an additional 90 minutes. The ion exchange resin was then removed from the acetal-containing reaction mixture products by filtration.

A gas liquid chromatographic analysis of the reaction mixture product obtained revealed the composition shown in Table I.

TABLE I

| Component | Weight Percent |
| --- | --- |
| Methanol | 14.02 |
| 2-Methoxy-3,4-dihydropyran | 1.50 |
| cis-2,6-Dimethoxy tetrahydropyran | 31.61 |
| trans-2,6-Dimethoxy tetrahydropyran | 6.76 |
| 5,5-Dimethoxypentanal | 31.61 |
| 1,1,5,5-Tetramethoxypentane | 14.50 |

A mixture of acids containing 1.9 kilograms of oxalic acid and 1.6 kilograms of boric acid was added to the acetal reaction mixture product and mixed to homogeneity and solution by rolling the drums. The drums were then stored at 60° C. for 26 days. There was no significant change in the acid-containing composition after this storage period. After this 26 day storage period, a portion of the acid-containing mixture was mixed with water to obtain a 35 weight percent solution. Within 2 hours the mixture was converted to a 16 weight percent solution of glutaraldehyde which represented a conversion of 80.5 percent.

EXAMPLE 3

To a mixture of 66 grams of methanol and 0.5 grams of concentrated sulfuric acid as catalyst there was added 236 grams of 2-methoxy-3,4-dihydropyran. The mixture was reacted as in Example 1 and then neutralized by the addition of 1 gram of sodium acetate. The acetal product mixture was stripped to remove the excess methanol and gas liquid chromatographic analysis of the resultant product indicated the composition shown in Table II.

TABLE II

| Component | Weight Percent |
| --- | --- |
| cis/trans-2,6-Dimethoxy tetrahydropyran | 67.1 |
| 5,5-Dimethoxypentanal | 17.0 |
| 1,1,5,5-Tetramethoxypentane | 7.0 |
| Glutaraldehyde | 6.9 |

Sixty-five grams of this mixture was mixed with 0.265 grams of glacial acetic acid to give a homogeneous solution, and stored at 60° C. for 30 days without any noticeable change. After this storage period, 10 grams of the mixture was added to 90 grams of distilled water resulting in a heterogeneous solution with a pH of 3.2. The solution was stirred at 25° C. and analyzed at 3 hour intervals. After 24 hours, gas liquid chromatographic analysis showed complete conversion of the acetals and pyrans to glutaraldehyde.

EXAMPLE 4

There was charged to a reaction vessel 114 grams of 2-methoxy-3,4-dihydropyran, 93 grams of ethylene glycol and 10 grams of Amberlyst-15 ® resin as catalyst. The mixture was stirred by a magnetic stirrer until the exotherm had ceased and then for an additional 60 minutes. The catalyst was removed by filtration. To the acetal reaction product there was added 1.4 grams of an equimolar boric acid-oxalic acid mixture to produce a storage stable composition. Water was then added to the composition to form a 35 weight percent solution and the solution was stirred for 3 hours; at the end of this period gas liquid chromatographic analysis showed a 90-95 percent conversion of the acetals and pyrans to glutaraldehyde.

EXAMPLE 5

Twenty-five grams of 1,1,5,5,-tetramethoxypentane was mixed with 46 grams of distilled water containing 0.2 gram of an equimolar mixture of oxalic acid and boric acid. The mixture was stirred for 2 hours at 25° C.-30° C. after which a gas liquid chromatographic analysis showed a 90 percent conversion of the 1,1,5,5-tetramethoxypentane to glutaraldehyde. This example shows that there need not be a mixture of glutaraldehyde acetals present to have an effective conversion to glutaraldehyde by hydrolysis. Only one acetal, in this example 1,1,5,5-tetramethoxypentane, is sufficient.

EXAMPLE 6

Water was added to 2,6-dimethoxy tetrahydropyran and the aqueous solution was allowed to stand for 6 hours. Then the biocidal activity of this aqueous solution was determined using the two measures of biocidal activity described below:

Zone of Inhibition—A disc containing the biocide is placed in the center of an inoculated petri dish and incubated for 24 hours at 37.5° C. The activity of the biocide is related to the diameter of the no growth area. The zone diameter is reported in millimeters and is the average of duplicate tests.

Plate Count—Microorganisms are in contact with the biocidal agent for thirty minutes before being plated for count. The number reported is the average of two tests. Counts are made after 24 hours of incubation at 37.5° C.

The inoculum employed in this example was Sarcina lutea-ATCC No. 9341. Comparative tests were also run with glutaraldehyde as the biocide. The results are shown in Table III.

TABLE III

| Compound | Initial pH | Concentration (ppm) | Zone of Inhibition (mm) | Plate Count |
|---|---|---|---|---|
| 2,6-Dimethoxy tetrahydropyran | 3.0 | 0 | 0 | TNTC* |
|  | 3.0 | 500 | 0 | 135 |
|  | 3.0 | 1000 | 13.7 | 0 |
|  | 3.0 | 5000 | 18.7 | 0 |
| Glutaraldehyde | 6.8 | 500 | 0 | 0 |
|  | 6.8 | 1000 | 14 | 0 |
|  | 6.8 | 5000 | 20.7 | 0 |

*Too Numerous To Count

This example shows that the compositions of this invention are effective biocides and have biocidal activity comparable to that of glutaraldehyde.

What is claimed is:

1. A storage stable composition comprising (I) at least one member selected from the group consisting of 2,6-dialkoxy tetrahydropyran, 5,5-dialkoxypentanal, 1,1,5,5-tetraalkoxypentane, or mixtures thereof and (II) from 0.25 to 2.5 weight percent, based on the weight of component I, of a soluble acid, wherein said alkoxy moieties contain from 1 to 3 carbon atoms.

2. A composition as claimed in claim 1, wherein component I is a mixture of 2,6-dimethoxy tetrahydropyran, 5,5-dimethoxypentanal, and 1,1,5,5-tetramethoxypentane.

3. A composition as claimed in claim 1, wherein component I is 1,1,5,5-tetramethoxypentane.

4. A composition as claimed in claim 1, wherein component II is oxalic acid.

5. A composition as claimed in claim 1, wherein component II is acetic acid.

6. A composition as claimed in claim 1, wherein component II is a mixture of oxalic acid and boric acid.

7. A composition as claimed in claim 2, wherein component II is oxalic acid.

8. A composition as claimed in claim 2, wherein component II is a mixture of oxalic acid and boric acid.

* * * * *